US006365351B1

(12) United States Patent
Iversen

(10) Patent No.: US 6,365,351 B1
(45) Date of Patent: Apr. 2, 2002

(54) NON-INVASIVE METHOD FOR DETECTING TARGET RNA

(75) Inventor: Patrick L. Iversen, Corvallis, OR (US)

(73) Assignee: AVI BioPharma, Inc., Corvallis, OR (US)

( * ) Notice: Subject to any disclaimer, the term of this patent is extended or adjusted under 35 U.S.C. 154(b) by 0 days.

(21) Appl. No.: 09/493,494

(22) Filed: Jan. 28, 2000

Related U.S. Application Data

(60) Provisional application No. 60/117,846, filed on Jan. 29, 1999.

(51) Int. Cl.$^7$ ............... C12Q 1/68; C07H 21/00; C07H 21/02; C07H 21/04
(52) U.S. Cl. ............... 435/6; 435/91.1; 435/455; 536/23.1; 536/24.5; 536/25.3; 536/25.32; 536/31
(58) Field of Search ............... 435/6, 91.1, 455; 536/23.1, 24.3, 24.31, 24.32, 24.5, 25.3, 25.32, 31; 514/44

(56) References Cited

U.S. PATENT DOCUMENTS

| | | | |
|---|---|---|---|
| 5,627,030 A | * 5/1997 | Pandian et al. | ................ 435/6 |
| 5,656,612 A | 8/1997 | Monia | |
| 5,756,476 A | * 5/1998 | Epstein et al. | ................ 514/44 |
| 5,827,661 A | * 10/1998 | Blais | ............................ 435/6 |
| 5,843,684 A | 12/1998 | Levine et al. | ............... 435/7.23 |
| 5,877,309 A | * 3/1999 | McKay et al. | ............. 536/24.5 |
| 6,013,639 A | * 1/2000 | Peyman et al. | ................ 514/44 |

FOREIGN PATENT DOCUMENTS

| WO | WO 99/02167 | 1/1999 |
|---|---|---|

OTHER PUBLICATIONS

Brett P. Monia et al., Evaluation of 2'–Modified Oligonucleotides Containing 2'–Deoxy Gaps as Antisense Inhibitors of Gene Expression, The Journal of Biological Chemistry, vol. 268, No. 19, Issued of July 5, pp. 14514–14522, 1993.*
Cross, N.C.P., "Assessing residual leukaemia" *Baillière's Clinical Haematology* 10 (2):389–403 (1997).

* cited by examiner

*Primary Examiner*—Andrew Wang
*Assistant Examiner*—Jane Zara
(74) *Attorney, Agent, or Firm*—Linda R. Judge; Perkins Coie LLP

(57) ABSTRACT

The present invention provides a method for targeting a particular mRNA sequence in vivo by oral administration of a morpholino antisense compound having uncharged phosphorus-containing backbone linkages. Also disclosed is a non-invasive method of detecting and quantitating the in vivo presence of RNA containing one or more selected target sequences. The method includes administering to a subject a nuclease-resistant antisense oligomer which hybridizes by Watson-Crick base pairing to a region of the target RNA with a Tm substantially greater than 37° C. The oligomer is able to complex intracellularly with target RNA, and is released from intracellular sites as a nuclease-resistant heteroduplex, which can then be measured in a body fluid sample, e.g., urine.

3 Claims, 3 Drawing Sheets

NON-INVASIVE METHOD FOR DETECTING TARGET RNA

This application claims priority to U.S. Provisional application Serial No. 60/117,846, filed Jan. 29, 1999 expressly incorporated by reference herein.

FIELD OF THE INVENTION

The present invention relates to methods for effective targeting of mRNA in vivo in a subject, by oral administration of a nuclease-resistant morpholino antisense compound having uncharged phosphorus-containing backbone linkages. The invention further relates to methods and kits for detection of base-specific intracellular binding events involving one or more target RNAs in a subject, wherein a heteroduplex comprising a target RNA and an antisense oligomer is detected in a body-fluid sample taken from the subject.

BACKGROUND OF THE INVENTION

Many diseases and other medical conditions are characterized by the presence of undesired DNA or RNA, which may be in certain instances single stranded and in other instances in double stranded. These diseases and conditions can be treated using the principles of antisense therapy which includes targeting a specific DNA or RNA target sequence through complementarity or through another specific binding means.

In therapeutic applications, antisense oligomers formulated for oral administration have met with limited success, which in general is attributed to the effects ubiquitous nucleases present in vivo and to the overall charge of the molecules which limits their ability to get into cells.

Numerous references directed to enhanced oral delivery of such antisense oligonucleotides for the diagnosis and treatment of disease may be found in the literature.

Diagnosis and monitoring of various disease conditions is accomplished by an analysis of peptides, proteins, antibodies or nucleic acids associated with the condition.

Genetic analysis of individuals usually focuses on two types of information: The first is analysis of mutations associated with various genetic diseases, e.g., cystic fibrosis, Huntington's disease, and certain cancers known to be associated with genetic mutations, e.g., breast cancer. The second involves the analysis of relative levels of expression of genes under certain conditions,. e.g., in response to drug treatment, in various diseases or conditions, or differences in levels of gene expression among different tissues.

Currently, genetic analyses of this type are carried out ex vivo, typically by obtaining a tissue of blood sample from an individual, and analyzing genomic DNA, cDNA or mRNA for the presence of absence of certain mutations or for elevated or depressed levels of gene expression. Diagnostic devices, e.g., gene chips, for detecting mutations or changes in level of expression are now available, and with new capabilities under development.

Similar methods may be employed to monitor the effect of therapeutic compounds on gene expression in individuals. That is, following compound administration, a tissue biopsy or blood sample may be obtained from the treated patient to determining the effect of the compound on expression of one or more targeted genes.

Although analysis of mutations and levels of gene expression by these in vivo methods has the capability of yielding important information about gene makeup and drug response in an individual, the methods are many times impractical, expensive and/or unable to provide the desired information. For example, it is generally not practical to biopsy an individual's tissue to monitor gene expression, both because of the difficulty and risk to patient of obtaining a tissue sample, and because of the expense of working up a tissue sample for analysis.

It would therefore be highly desirable to be able to target gene mutations and monitor levels of gene expression, or gene expression in response to therapeutic agents by methods that do not require obtaining tissue or cellular samples from an individual, nor and isolating and measuring nucleic acids samples obtained from such cells or tissue.

SUMMARY OF THE INVENTION

The present invention addresses a deficiency in the prior art by providing a method for effective targeting of mRNA in vivo in a subject, by oral administration of a nuclease-resistant morpholino antisense compound having uncharged phosphorus-containing backbone linkages in a manner which results in modulated expression of the gene product encoded by the mRNA target.

In one aspect, the antisense compound preferably has a length of about 8 to 40 bases, more preferably 12 to 25 bases.

In another aspect, the antisense compound preferably has intersubunit linkages selected from the group consisting of the structures presented in FIGS. 2A–2E, and exemplified particularly by the phosphorodiamidate linkage represented at FIG. 2B, where X=NH$_2$, Y=O, and Z=O.

In an further aspect, the morpholino antisense compound contains a targeting base sequence that is complementary to a region that spans the translational start codon of a selected target gene.

A preferred target gene for an orally administered antisense oligomer of the invention is a gene associated with a proliferative disorder, e.g., cancer. An exemplary sequence is the one identified by SEQ ID NO: 2.

In a related aspect, the invention provides a method of detecting, the occurrence of a base-specific intracellular binding event involving a target RNA in a subject, by performing the steps of (a) administering to the subject a morpholino antisense compound including a targeting base sequence that is complementary to a region that spans the start codon of a selected gene, and uncharged, phosphorous-containing intersubunit linkages, in an amount effective to hybridize to a region of the target RNA with a Tm substantially greater than 37° C., (b) taking a sample of a body fluid from the subject at a selected time after administering the oligonucleotide, and (c) detecting the presence of a nuclease-resistant heteroduplex composed of the antisense oligonucleotide and the target RNA region in the sample.

In practicing the method, it is preferred that the antisense oligomer have a length of about 8 to 40 bases and be effective following oral administration.

The methods of the invention provide for detection of antisense oligomer:RNA heteroduplexes in a body fluid such as urine, saliva, plasma, or blood, preferably urine.

In one aspect, detection of the heteroduplex is accomplished by reacting the sample with an antibody specific for the heteroduplex, and detecting the presence of the antibody-heteroduplex conjugate.

In other cases, the methods of the invention provide an antisense oligomer comprising a reporter molecule such that detection of antisense oligomer:RNA heteroduplexes is accomplished by detecting the presence of the reporter molecule associated with the heteroduplexes.

The invention further provides diagnostic methods for assessing the biological condition of a subject, wherein the biological condition is associated with expression of a target gene and the methods are used to detect changes in RNA associated with expression of the target gene.

In one preferred application, the method may be used to detect changes in expression of a target gene in response to a therapeutic agent in the subject, wherein the target RNA is mRNA produced by expression of a selected gene, e.g., a gene associated with a known disease state.

The invention is applicable to single or multiple administrations of nuclease-resistant antisense oligomers for therapeutic and or diagnostic applications.

The invention also provides kits for detecting the occurrence of a base-specific intracellular binding event involving a target RNA in a subject comprising a nuclease-resistant antisense oligomer complementary to a target RNA which hybridizes to the target with a Tm substantially greater than 37° C., and a means for detecting a heteroduplex formed between the antisense oligomer and the target RNA.

These and other objects and features of the invention will become more fully apparent when the following detailed description is read in conjunction with the accompanying drawings.

BRIEF DESCRIPTION OF THE DRAWINGS

FIG. 1 shows several preferred subunits having 5-atom (A), six-atom (B) and seven-atom (C–E) linking groups suitable for forming polymers.

DETAILED DESCRIPTION OF THE INVENTION

I. Definitions

The terms below, as used herein, have the following meanings, unless indicated otherwise:

As used herein, the term "oligonucleotide" is used interchangeably with the term "antisense oligonucleotide" and refers to an oligomer having a sequence of nucleotide bases and a subunit-to-subunit backbone that allows the antisense oligomer to hybridize to a target sequence in an RNA by Watson-Crick base pairing, to form an RNA:oligomer heteroduplex within the target sequence. The oligomer may have exact sequence complementarity to the target sequence or near complementarity. These antisense oligomers may block or inhibit translation of the mRNA containing the target sequence, or inhibit gene transcription, where the oligonucleotide is a double-stranded binding agent.

As used herein, the term "antisense oligomer composition" refers to a composition comprising one or more antisense oligomers for use in the RNA detection methods of the present invention. In some cases, such an "antisense oligomer composition" comprises a plurality of antisense oligomers.

As used herein, the terms "compound", "agent", "oligomer" and "oligonucleotide" may be used interchangeably with respect to the antisense oligonucleotides of the invention. The terms refer to a sequence of nucleotide bases and a subunit-to-subunit backbone that allows the antisense oligomer to hybridize to a target sequence in an RNA by Watson-Crick base pairing, to form an RNA:oligomer heteroduplex with the target sequence. The oligomer may have exact sequence complementarity to the target sequence or near complementarity. Such antisense oligomers may block or inhibit translation of the mRNA containing the target sequence, or inhibit gene transcription, may bind to double-stranded or single stranded sequences, and may be said to be "directed to" a sequence with which it hybridizes.

Exemplary structures for antisense oligonucleotides for use in the invention include the morpholino subunit types shown in FIGS. 1A–E. It will be appreciated that a polymer may contain more than one linkage type.

Figure 1A:
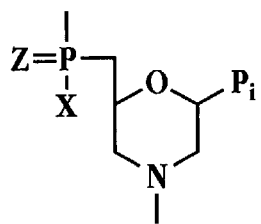
FIGS. 1A–1E.
Figure 1B:
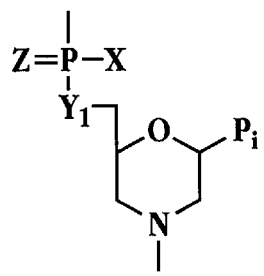
Figure 1C:
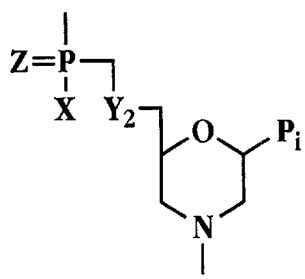
Figure 1D:
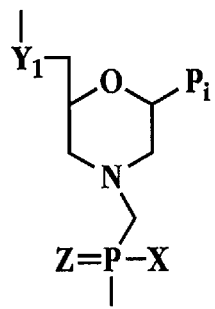
Figure 1E:
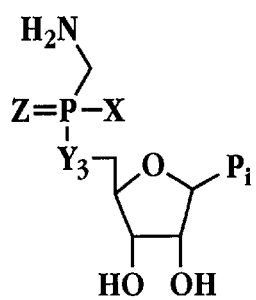
Figure 2A:
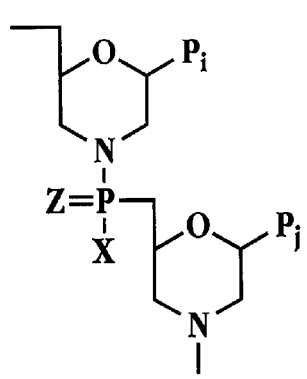
FIGS. 2A–E show the repeating subunit segment of exemplary morpholino oligonucleotides, designated 2A through 2E, constructed using subunits A–E, respectively, of FIG. 1.

Subunit A in FIG. 1 contains a 1-atom phosphorous-containing linkage which forms the five atom repeating-unit backbone shown at in FIG. 2A, where the morpholino rings are linked by a 1-atom phosphonamide linkage.

Figure 2B:
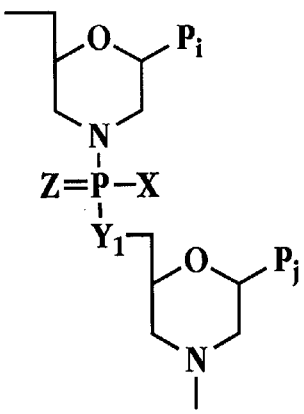

Subunit B in FIG. 1 is designed for 6-atom repeating-unit backbones, as shown at B—B, in FIG. 2B. In structure B, the atom Y linking the 5' morpholino carbon to the phosphorous group may be sulfur, nitrogen, carbon or, preferably, oxygen. The X moiety pendant from the phosphorous may be any of the following: fluorine; an alkyl or substituted alkyl; an alkoxy or substituted alkoxy; a thioalkoxy or substituted thioalkoxy; or, an unsubstituted, monosubstituted, or disubstituted nitrogen, including cyclic structures.

Figure 2C:
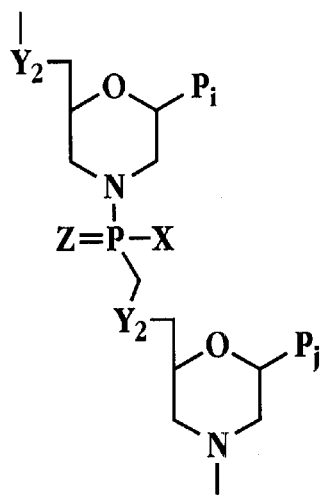
Figure 2D:
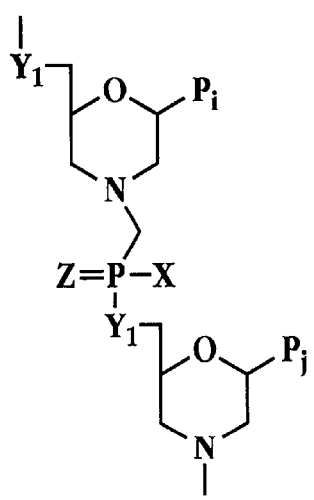
Figure 2E:
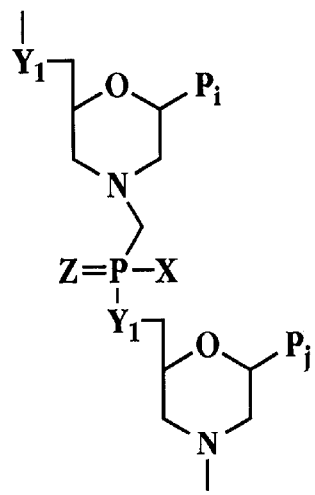

Subunits C–E in FIG. 1 are designed for 7-atom unit-length backbones as shown in FIGS. 2C through 2E. In Structure C, the X moiety is as in Structure B and the moiety Y may be a methylene, sulfur, or preferably oxygen. In Structure D the X and Y moieties are as in Structure B. In Structure E, X is as in Structure B and Y is O, S, or NR. In all subunits depicted in FIGS. 1A–E, Z is O or S, and $P_i$ or $P_j$ is adenine, cytosine, guanine or uracil.

As used herein, a "morpholino oligomer" refers to a polymeric molecule having a backbone which supports bases capable of hydrogen bonding to typical polynucleotides, wherein the polymer lacks a pentose sugar backbone moiety, and more specifically a ribose backbone linked by phosphodiester bonds which is typical of nucleotides and nucleosides, but instead contains a ring nitrogen with coupling through the ring nitrogen. A preferred "morpholino" oligonucleotide is composed of morpholino subunit structures of the form shown in FIG. 2B, where (i) the structures are linked together by phosphorous-containing linkages, one to three atoms long, joining the morpholino nitrogen of one subunit to the 5' exocyclic carbon of an adjacent subunit, and (ii) $P_i$ and $P_j$ are purine or pyrimidine base-pairing moieties effective to bind, by base-specific hydrogen bonding, to a base in a polynucleotide.

As used herein, the term "PMO" refers to a phosphodiamidate morpholino oligomer, as further described below, wherein the oligomer is a polynucleotide of about 8–40 bases in length, preferably 12–25 bases in length. This preferred aspect of the invention is illustrated in FIG. 2B, which shows two such subunits joined by a phosphorodiamidate linkage.

This preferred aspect of the invention is illustrated in FIG. 2B, which shows two such subunits joined by a phosphorodiamidate linkage. Morpholino oligonucleotides (including antisense oligomers) are detailed, for example, in co-owned U.S. Pat. Nos. 5,698,685, 5,217,866, 5,142,047, 5,034,506, 5,166,315, 5,185,444, 5,521,063, and 5,506,337, all of which are expressly incorporated by reference herein.

As used herein, a "nuclease-resistant" oligomeric molecule (oligomer) is one whose backbone is not susceptible to nuclease cleavage of a phosphodiester bond. Exemplary nuclease resistant antisense oligomers are oligonucleotide analogs, such as phosphorothioate and phosphate-amine DNA (pnDNA), both of which have a charged backbone, and methyl-phosphonate, morpholino, and peptide nucleic acid (PNA) oligonucleotides, all of which have uncharged backbones.

As used herein, an oligonucleotide or antisense oligomer "specifically hybridizes" to a target polynucleotide if the oligomer hybridizes to the target under physiological conditions, with a Tm substantially greater than 37° C., preferably at least 50° C., and typically 6° C.–8° C. or higher. Such hybridization preferably corresponds to stringent hybridization conditions, selected to be about 10° C., and preferably about 5° C. lower than the thermal melting point (T[m]) for the specific sequence at a defined ionic strength and pH. At a given ionic strength and pH, the T[m] is the temperature at which 50% of a target sequence hybridizes to a complementary polynucleotide.

Polynucleotides are described as "complementary" to one another when hybridization occurs in an antiparallel configuration between two single-stranded polynucleotides. A double-stranded polynucleotide can be "complementary" to another polynucleotide, if hybridization can occur between one of the strands of the first polynucleotide and the second. Complementarity (the degree that one polynucleotide is complementary with another) is quantifiable in terms of the proportion of bases in opposing strands that are expected to form hydrogen bonds with each other, according to generally accepted base-pairing rules.

As used herein, the term "cancer-specific antigen" refers to an antigen that is expressed by cancer cells and not by normal or non-cancer cells.

As used herein, the term "cancer-associated antigen", refers to an antigen that is expressed by cancer cells, but may also be expressed by normal or non-cancer cells, exemplified herein by c-myc.

As used herein, the term "c-myc antisense oligomer" refers to a nuclease-resistant antisense oligomer having high affinity (i.e., "specifically hybridizes") to a complementary or near-complementary c-myc nucleic acid sequence.

As used herein, a first sequence is an "antisense sequence" with respect to a second sequence if a polynucleotide whose sequence is the first sequence specifically binds to a polynucleotide whose sequence is the second sequence.

As used herein, a "base-specific intracellular binding event involving a target RNA" refers to the specific binding of an oligomer with a target RNA sequence inside a cell. The base specificity of such binding is sequence specific. For example, a single-stranded polynucleotide can specifically bind to a single-stranded polynucleotide that is complementary in sequence.

As used herein, "nuclease-resistant heteroduplex" refers to a heteroduplex formed by the binding of an antisense oligomer to its complementary target, which is resistant to in vivo degradation by ubiquitous intracellular and extracellular nucleases.

As used herein, the term "target", relative to an mRNA or other nucleic acid sequence, refers to an mRNA or other nucleic acid sequence which is preferentially expressed in hematopoietic stem cells. Preferentially expressed means the target mRNA is derived from a gene expressed in hematopoietic stem cells to a greater extent than the same gene is expressed in more differentiated cells, or expression specific to hematopoietic stem cells and not detectable in more differentiated cells.

As used herein, the term "modulating expression" relative to oligonucleotides refers to the ability of an antisense oligomer to either enhance or reduce the expression of a given protein by interfering with the expression, or translation of RNA. In the case of enhanced protein expression, the antisense oligomer may block expression of a suppressor gene, e.g., a tumor suppressor gene. In the case of reduced protein expression, the antisense oligomer may directly block expression of a given gene, or contribute to the accelerated breakdown of the RNA transcribed from that gene.

As used herein, "effective amount" relative to an antisense oligomer refers to the amount of antisense oligomer administered to a mammalian subject, either as a single dose or as part of a series of doses, that is effective to specifically hybridize to all or part of a selected target sequence forming a heteroduplex between the target RNA and the antisense oligomer which may subsequently be detected in a body fluid of the subject.

As used herein "treatment" of an individual or a cell is any type of intervention in an attempt to alter the natural course of the individual or cell. Treatment includes, but is not limited to, administration of e.g., a pharmaceutical composition, and may be performed either prophylactically, or subsequent to the initiation of a pathologic event or contact with an etiologic agent.

As used herein, the term "body fluid" encompasses a variety of sample types obtained from a subject including, urine, saliva, plasma, blood, spinal fluid, and other liquid sample of biological origin, and may refer include cells or cell fragments suspended therein, or the liquid medium and its solutes.

The term "relative amount" is used where a comparison is made between a test measurement and a control measurement. The relative amount of a reagent forming a complex in a reaction is the amount reacting with a test specimen, compared with the amount reacting with a control specimen. The control specimen may be run separately in the same assay, or it may be part of the same sample (for example, normal tissue surrounding a malignant area in a tissue section).

As used herein, the term "proliferative disorder" refers to a condition characterized by abnormal cell proliferation, and may apply to malignant as well as non-malignant cell populations which differ from surrounding tissue both morphologically and/or genotypically.

As used herein, the terms "tumor" and "cancer" refer to a cell that exhibits a loss of growth control and forms unusually large clones of cells. Tumor or cancer cells generally have lost contact inhibition and may be invasive and/or have the ability to metastasize.

As used herein, the term "improved therapeutic outcome" relative to a cancer patient refers to a slowing or diminution of the growth of cancer cells or a solid tumor, or a reduction in the total number of cancer cells or total tumor burden.

II. Methods of the Invention

The methods of the present invention provide a means for effective oral administration of a class of morpholino antisense oligonucleotides which are effective to bind with high affinity to a complementary or near-complementary target RNA.

The invention further provides a method of detecting the occurrence of a base-specific intracellular binding event involving a target RNA. The invention is based on the discovery that a nuclease-resistant antisense morpholino oligomer, or more generally, a nuclease-resistant morpholino oligomer, capable of binding with high affinity to a complementary or near-complementary target RNA sequence can be administered to an individual, and subsequently detected in a body-fluid sample, e.g., in the urine, in the form of a nuclease-resistant heteroduplex of the antisense oligomer and the target RNA.

Although the mechanism underlying the discovery is not part of the claimed invention, the discovery does suggest that an orally administered antisense oligomer is able to (i) migrate to and enter cells in the body, (ii) bind with high-affinity by Watson-Crick base pairing to complementary or near-complementary target regions of a target RNA, to form a heteroduplex with the target region of the RNA, and (iii) block the expression thereof.

In the detection method of the invention, the discovery suggests that once administered the antisense oligomer is able to (i) migrate to and enter cells in the body, (ii) bind with high-affinity by Watson-Crick base pairing to complementary or near-complementary target regions of a target RNA, to form a heteroduplex with the target region of the RNA, (iii) protect the heteroduplex region of the RNA from nuclease degradation, (iv) be expelled from the cells into the bloodstream in the form of a nuclease-resistant heteroduplex, and (v) survive in the bloodstream, in sufficient amount, for detection in a body fluid, e.g., blood, urine, saliva, etc.

A. Antisense Oligomer Compounds and Compositions Targets For Orally Delivered Morpholino Antisense Oligonucleotides Preferred targets for use in the methods of the invention include RNAs that are (1) developmentally and/or tissue regulated; (2) up- or down-regulated in various disease states, in particular proliferative disorders; (3) up- or down-regulated in response to environmental stimuli; and (4) altered by therapeutic regimes or the expression of which is altered by such therapeutic regimes.

Certain genetic diseases are characterized by the presence of genes which are not present in normal tissue. Other diseased conditions are characterized by the altered expression of RNAs or RNA translation products (i.e. peptides or proteins) which are not expressed in normal cells. Some disease states are characterized by the absence of certain genes or portions of genes, or the absence or alteration of expression of gene products or proteins.

The methods of the present invention may be used to modulate and/or monitor the expression of genes which are correlated with disease conditions, in particular genetic diseases. For example, periodic administration of an antisense oligomer associated with particular disease states and monitoring of antisense oligomer:RNA heteroduplexes in the urine of subjects may be used to detect expression of genes known by those of skill in the art to be associated with particular disease states. Accordingly, the methods of the invention provide a means for early intervention in such disease states, a method administering therapeutic oligonucleotides and for monitoring the presence of RNA(s) associated with the particular disease state. Exemplary disease states include cystic fibrosis, cancers, e.g., breast cancer, Huntington's disease and other known genetic diseases.

The methods of the invention find further utility in screening for any of a plurality of medical conditions by administering a plurality of antisense oligomers, each specific for a different expressed RNA which is in itself specific to a particular disease state or medical condition.

Two types of altered gene expression have been observed to take place, together or independently, in different cancer cells [Bishop, Cell (1991) 64:235–248; U.S. Pat. No. 5,776, 683]. In the first type there is decreased expression of recessive tumor suppressor genes, that apparently act to prevent malignant growth. In the second type there is increased expression of dominant genes, such as oncogenes, that act to promote malignant growth, or to provide some other phenotype critical for malignancy. Alteration in the expression of either type of gene is a potential diagnostic indicator which may be monitored by the administration of antisense oligomers to a subject which are specific to, e.g., the tumor suppressor gene or oncogene, followed by detection of antisense oligomer:RNA heteroduplexes in a body fluid of the subject.

The alterations in cellular function which are observed in cancer arise from a wide range of sources. In some cases the change is triggered by cellular factors, in other situations the alteration brings about a malignant transformation. For example, a mutation in a normal gene can result in the malignant transformation of a cell such as when the proto-oncogene ras is transformed by a point mutation to become an oncogene. The simian virus 40 (SV40) T-antigen is another oncogene expression product that displays a wide range of functions. [Fanning, E., and Knippers, R., Annul. Rev. Biochem. 61:55–85 (1993)]; U.S. Pat. No. 5,843,737]. Mutations of proto-oncogenes in somatic cells are increasingly being recognized as significant in the induction of human cancers. Some examples of oncogenes formed by such mutations include: neu, neu/erbB2, fes, fos, myc, myb, fins, Ha-ras, and Ki-ras. The mutations that convert proto-oncogenes to oncogenes are often point mutations. [See, U.S. Pat. No. 5,843,684.]. The RNAs formed by expression of such mutated genes may serve as templates for the design of antisense oligomers for use in the methods of the present invention.

Other targets for evaluation of RNA expression using the methods of the invention include antisense oligomers specific to the RNAs which have been correlated with cancer cells that are resistant to a wide variety of chemotherapeutic drugs. Exemplary targets include P-glycoprotein, the multidrug resistance-associated protein (MRP), and the lung resistance protein (LRP) [See, e.g., Stein, U. et al., J Natl Cancer Inst 89: 807–813 (1997).]

In one aspect, the oral delivery methods of the invention may be used to deliver an antisense oligonucleotide to a subject, e.g., a cancer patient, as part of a therapeutic regimen. Exemplary targets for such treatment include a morpholino oligomer antisense to c-myc, exemplified by the sequence presented as SEQ ID NO:2.

The sequences for numerous oncogenes, tumor suppressor genes and other RNAs associated with cancer and other disease states are known in the art, are readily available in public databases, and may be used to design antisense oligomers for treatment and detection thereof.

Tumor-suppressor genes, such as the p53 gene, the retinoblastoma gene and the Wilm's tumor gene are also associated with malignant transformation. The phenotype is recessive since, when both alleles are mutated, the absence of a tumor suppressor gene results in an enhancement of tumorigenesis. The normal expression of these genes typically prevents unchecked cellular growth, while their mutation allows cell growth to go unchecked, thereby resulting in malignant transformation of a cell. Considerable attention has focused on all of the members of this family, particularly p53, because of its complex role in cellular regulation. [Science 262:1958–1961 (1993); U. S. Pat. No. 5,843,684]. Mutations in this gene have been associated with a wide range of human tumors, including the bladder, brain, breast, cervix, colon, esophagus, larynx, liver, lung, ovary, pancreas, prostate, skin, stomach, and thyroid. Accordingly, p53 may be targeted by the oral delivery of morpholino antisense oligomers, as described herein.

Members of DNA repair systems are molecules that can also dramatically effect a cell, particularly the malignant transformation of a cell. For example, it was recently discovered that a mismatch repair system exists in humans [Fishel, R, et al., Cell 75:1027–1038 (1993); Leach, F. S., et al., Cell 75:1215–1225 (1993); and Parsons, R., Cell 75:1227–1236 (1993)). Members of this system include the human mismatch repair gene hMSH2. Mutations in these genes have been associated with a variety of cancers including hereditary non-polyposis colon cancer (HNPCC) (Aaltonen, L. A., Science 260:812–816 (1993)]. Accordingly, the methods of the invention find utility in monitoring such repair systems.

In addition, the methods of the present invention are useful to monitor a treatment strategy which seeks to reinstate the expression of suppressor genes, or reduce the expression of dominant genes, such as oncogenes. Preferred disease targets include, cancer, particularly cancers of the bladder, brain, breast, cervix, colon, esophagus, larynx, liver, lung, ovary, pancreas, prostate, skin, stomach, and thyroid.

An exemplary disease condition wherein the methods of the invention may be used is assessing the quality of remission in patients with chronic myeloid leukaemia (CML). The standard method currently used is cytogenetic analysis of bone marrow derived metaphases, fluorescence in situ hybridization (FISH) analyses of chromosomes to detect either the juxtaposition of oncogene sequences or the disruption of these genes, reverse-transcriptase polymerase chain reaction (RT-PCR) analysis to determine the presence or absence of oncogene (BCR-ABL) transcripts, and western blot analysis of cell lysates to determine the presence or absence of the BCR-ABL protein. Each of these techniques has particular advantages and pitfalls, and usually requires a biopsy or blood collection. Accordingly, these techniques are generally restricted to research laboratories and a need exists for a means to monitor the quality of remission in CML patients [Cross, N.C.P., Bailliere's Clin. Haematol. 2:389–403 (1997)].

The methods of the invention provide a non-invasive procedure for evaluating RNA expression and accordingly treating and/or monitoring disease conditions such as CML.

By providing an efficient and effective means to detect expressed RNA, the present invention provides advantages over methods for the detection of genes themselves in that genes may be overexpressed in cancer (or other disease states), without being duplicated or may be duplicated and remain quiescent.

In addition, the invention provides a means to detect or monitor altered expression of a gene which is not the tumor suppressor gene or oncogene itself, but expressed as a consequence of a disease condition, such as cancer. The evaluation of the expression of such genes may nonetheless be diagnostic and/or prognostic of the condition. For example, the epidermal growth factor receptor is overexpressed in 45% of breast cancer tumors [Klijn et al, Endocrine Rev. 13:3–17 (1992)], and the IGF-1 receptor is overexpressed in 50–93% of breast cancer tumors [Berns et al., Cancer Res. 52:1036–1039 (1992)].

It has been demonstrated that altered expression of growth factors may result in, or be the cause of a disease condition. For example, nerve growth factor and fibroblast growth factor have been shown to affect neuronal cell survival in animal models of Alzheimer's disease and therapies involving administration of nucleic acids encoding such growth factors are under investigation. [See, e.g., U.S. Pat. No. 5,580,859.]

The methods of the present invention may be used to evaluate the expression of factors which themselves regulate gene expression, such as proteins or other molecules which affect levels of mRNA produced by expression of a specific gene, and/or factors the expression of which is up- or down-regulated in various disease states. These factors include hormones, cytokines, intracellular messengers, transcription factors, carcinogens, among others.

The effect of antisense oligonucleotides on down-regulation of the expression of the bcl-2 protein, which has been correlated with small-cell lung cancer, is the subject of ongoing clinical trials. [See, e.g., Ziegler. A et al., [J Natl Cancer Inst 89: 1027–1036 (1997)]. The methods of the present invention may be used to monitor such trials, e.g. gene therapy trials, by periodic administration of antisense oligomers and monitoring of antisense oligomer:RNA heteroduplexes in the urine of patients participating in such studies. [See, e.g., U.S. Pat. No. 5,843,684.]

The methods of the invention may also be used to diagnose and monitor RNA splicing events. The splicing process involves the removal of introns (intervening, non-coding regions of DNA that are transcribed into RNA in the "primary transcript or "pre-mRNA), from pre-mRNA and subsequent joining of exons. Aberrant splicing may take place when there is a mutation in the pre-mRNA. (See, e.g., U.S. Pat. No. 5,627,274.) Antisense therapy has been used to correct such aberrant splicing. Accordingly, the methods of the invention may also be used to monitor the effect of such therapy.

The methods of the invention find further utility in monitoring the infection of a subject by any of a number of microorganisms and the effect of therapeutic intervention on such infection. More specifically, infection with particular viruses, bacteria or fungi may be diagnosed and therapy monitored by evaluating the expression of RNA associated with such infection using the methods of the invention. Characteristic nucleic acid sequences which are associated with a large number of infectious microorganisms are available in public databases and may serve as the basis for the design of specific antisense oligomers for use in the methods of the invention.

For example, typically viral infections (e.g., those caused by the expression of a latent virus such as CMV) are monitored by analysis of infected tissue or blood using immunofluorescence assays, polymerase chain reaction (PCR), and/or enzyme-linked immunosorbent assay (ELISA). The present invention provides the advantage of a method for routine monitoring of active infection with a non-invasive procedure by administering to a subject an antisense oligomer specific to a viral RNA associated with infection and subsequent analysis of heteroduplexes comprising that oligomer in the urine of the subject.

B. Advantages Of Morpholino Antisense

A morpholino subunit differs from a nucleoside or nucleotide subunit in that (i) it lacks a pentose sugar backbone moiety, and more specifically a ribose backbone moiety, (ii) the backbone moiety in a morpholino-based subunit group contains a ring nitrogen, and (iii) backbone coupling to the subunit in a morpholino-subunit polymer is through the ring nitrogen.

The important chemical properties of a morpholino-based subunit are the ability to be linked in a polymeric form by stable, uncharged backbone linkages, and the ability of the polymer so formed to hybridize with a complementary-base target nucleic acid, including target RNA, with high affinity.

Morpholino oligonucleotides are distinguished from other types of oligonucleotides by the type of inter-subunit linkage, and differ in the following ways.

Natural polynucleotides, linked by phosphodiester bonds, have relatively high binding affinities for complementary-strand DNA and RNA, as measured by the $T_m$ (melting temperature) of the two complementary strands. Under physiological conditions, a typical 20mer DNA strand has a $T_m$ of about 72° C. when paired with a complementary-strand DNA, and a $T_m$ of about 77° C. when paired with a complementary-strand RNA. Both strands of such duplexes have charged backbones.

Polynucleotides in which the charged phosphodiester linkages are replaced by other charged linkages, e.g., phosphorothioates or phosphorodithioates, show a significant loss in binding affinity to natural polynucleotides and require higher concentrations for cellular uptake than uncharged oligonucleotides containing the same number of nucleobases.

Polynucleotides in which the charged phosphodiester linkages are replaced by uncharged linkages, e.g., methylphosphonates, phosphotriesters, phosphoroamidates, and carbamates, all show a significant decrease in binding affinity with DNA or RNA when compared with a phosphodiester-linked polynucleotide.

Accordingly, oligonucleotides constructed of morpholino-based subunits linked-by optimal, uncharged linkages are preferred for high binding affinity when paired with complementary-strand RNA or DNA.

C. Exemplary c-myc Antisense Compound c-myc is a proto-oncogene which regulates cell growth and differentiation, is involved in the process of vascular remodeling, regulating smooth muscle cell proliferation and extracellular matrix synthesis, in addition to playing a role in apoptosis. Aberrant expression of c-myc is frequently observed in human cancer. Aberrant, constitutive or overexpression of c-myc has been associated with a number of human cancers including lung cancer, colorectal cancer, breast cancer, bladder cancer, leukemia, lung cancer, etc.

The myc proto-oncogenes have been described as transcription factors that directly regulate the expression of other genes, examples of which include ECA39, p53, ornithine decarboxylase (ODC), alpha-prothymosin and Cdc25A (Ben-Yosef, T., et al., *Oncogene* 17(2):165–71, 1998).

In vitro translation of several oncogene mRNAs has been shown to be successfully blocked by phosphodiester and/or phosphorothioate antisense oligonucleotides (c-myc: McManaway, et al., *Lancet* 335:808, 1990; Watson, et al., *Cancer Res.* 51:3996, 1991; bcl-2: Reed, et al., *Cancer Res.* 50:6565, 1990; myb: Calabrett, et al., *Proc. Natl. Acad. Sci. USA* 88:2351, 1991; bcr-ab: Szczylik, et al., *Science* 253:562 1991).

In accordance with the present invention, it has been discovered that an orally administered morpholino antisense compound having (i) from 8 to 40 nucleotides, including a targeting base sequence that is complementary to a region that spans the translational start codon of a selected gene, and (ii) uncharged, phosphorous-containing intersubunit linkages will hybridize to a target sequence contained within a target mRNA, under physiological conditions with a Tm substantially greater than 37° C. In vitro and animal-model studies conducted in support of the invention indicate that such an antisense compound (i) is taken up efficiently following oral administration; (ii) acts intracellularly to inhibit translation of the target mRNA, and (iii) is significantly more efficient, in such inhibition, than other types of antisense compounds, e.g., phosphorothioate antisense compounds.

The synthesis, structures, and binding characteristics of morpholino oligomers are detailed in above-cited U.S. Pat. Nos. 5,698,685, 5,217,866, 5,142,047, 5,034,506, 5,166, 315, 5,521,063, and 5,506,337, all of which are incorporated herein by reference. The antisense oligomers (compounds) of the present invention are composed of morpholino subunits of the form shown in the above cited patents, where (i) the morpholino groups are linked together by uncharged phosphorus-containing linkages, one to three atoms long, joining the morpholino nitrogen of one subunit to the 5' exocyclic carbon of an adjacent subunit, and (ii) the base attached to the morpholino group is a purine or pyrimidine base-pairing moiety effective to bind, by base-specific hydrogen bonding, to a base in a polynucleotide. The purine or pyrimidine base-pairing moiety is typically adenine, cytosine, guanine, uracil or thymine. Preparation of such oligomers is described in detail in U.S. Pat. No. 5,185,444 (Summerton and Weller, 1993), which is hereby incorporated by reference in its entirety. As shown in the reference, several types of nonionic linkages may be used to construct a morpholino backbone.

Exemplary backbone structures for antisense oligonucleotides of the invention include the β-morpholino subunit types shown in FIGS. 1A–E. It will be appreciated that a polynucleotide may contain more than one linkage type.

Subunit A in FIG. 1 contains a 1-atom phosphorous-containing linkage which forms the five atom repeating-unit backbone shown at A—A in FIG. 2, where the morpholino rings are linked by a 1-atom phosphoamide linkage.

Subunit B in FIG. 1 is designed for 6-atom repeating-unit backbones, as shown at B—B, in FIG. 2. In structure B, the atom Y linking the 5' morpholino carbon to the phosphorous group may be sulfur, nitrogen, carbon or, preferably, oxygen. The X moiety pendant from the phosphorous may be any of the following: fluorine; an alkyl or substituted alkyl; an alkoxy or substituted alkoxy; a thioalkoxy or substituted thioalkoxy; or, an unsubstituted, monosubstituted, or disubstituted nitrogen, including cyclic structures.

Subunits C–E in FIG. 1 are designed for 7-atom unit-length backbones as shown for C—C through E—E in FIG. 2. In Structure C, the X moiety is as in Structure B and the moiety Y may be a methylene, sulfur, or preferably oxygen. In Structure D the X and Y moieties are as in Structure B. In Structure E, X is as in Structure B and Y is O, S, or NR. In all subunits depicted in FIGS. 1A–E, Z is O or S, and $P_i$ or $P_j$ is adenine, cytosine, guanine or uracil.

A preferred "morpholino" oligonucleotide is composed of morpholino subunit structures of the form shown in FIG. 2B, where (i) the structures are linked together by phosphorodiamidate containing linkages, one to three atoms long, joining the morpholino nitrogen of one subunit to the 5' exocyclic carbon of an adjacent subunit, (ii) $P_i$ and $P_j$ are purine or pyrimidine base-pairing moieties effective to bind, by base-specific hydrogen bonding, to a base in a polynucleotide, and $X=NH_2$, $Y=O$, and $Z=O$.

As noted above, the oligonucleotide compound has a sequence which spans the start codon of a target mRNA, meaning the compound contains a sequence complementary to a region of target RNA containing the AUG mRNA translational start site and adjacent 5' and 3' base(s). The region of the mRNA against which the compound is directed is also referred to herein as the target sequence. The mRNA may be a preprocessed or post-processed mRNA.

The compound is designed to hybridize to the target mRNA, under physiological conditions with a Tm substantially greater than 37° C., e.g., at least 50° C. and preferably 60° C.–80° C. Although the compound is not necessarily 100% complementary to the target sequence, it is effective to stably and specifically bind to the target sequence such that expression of the target sequence, is modulated. The appropriate length of the oligomer to allow stable, effective binding combined with good specificity is about 8 to 40 nucleotide base units, and preferably about 12 to 25 base units. Mismatches, if present, are less destabilizing toward the end regions of the hybrid duplex than in the middle. Oligomer bases that allow degenerate base pairing with target bases are also contemplated, assuming base-pair specificity with the target is maintained. Preferably, the compound contains an internal 3-base codon complementary to the AUG site, and one or more bases 5' and 3' to the start site. One exemplary compound spans the c-myc start site sequence is presented as SEQ ID NO:2 and has the base sequence: 5'-ACG TTG AGG GGC ATC GTC GC-3'. In addition to spanning the c-myc start site, the compound has a solubility in aqueous medium of greater than about 30 mg/ml.

The solubility of the antisense compound, and the ability of the compound to resist precipitation on storage in solution, can be further enhanced by derivatizing the oligomer with a solubilizing moiety, such as a hydrophilic oligomer, or a charged species.

The effectiveness of a given antisense sequence in forming a heteroduplex with the target RNA may be determined by screening methods known in the art. For example, the oligomer is incubated with a cell culture expressing the target RNA, and the presence or absence of the heteroduplex is determined by techniques such as those set forth in below, or by monitoring the presence or absence of the encoded protein as determined by standard techniques such as ELISA or Western blotting. [See, for example, Pari, G. S. et al., *Antimicrob. Agents and Chemotherapy* 39(5): 1157–1161 (1995); Anderson, K. P. et al., *Antimicrob. Agents and Chemotherapy* 40(9):2004–2011 (1996).] It is generally desirable that non-specific binding of the oligomeric molecule to non-target sequences is limited.

Antisense oligomers for use in carrying out the method of the invention must have the following properties; (A) nuclease resistance, (B) the ability to hybridize with the complementary sequence of a target RNA with high affinity, that is, at a Tm substantially greater than 37° C., and (C) the ability to form nuclease-resistant oligomer:RNA heteroduplexes with the target RNA.

Although double-stranded DNA may be targeted by antisense molecules, mRNA transcribed from the relevant region of the gene is more generally targeted. Such mRNA contains, in addition to coding sequences, initiator or promoter sites, intron/exon junction sites, a 3'-untranslated region, and a 5'-untranslated region, which regions may also be targeted.

Candidate antisense oligomers are also evaluated, according to well known methods, for acute and chronic cellular toxicity, such as the effect on protein and DNA synthesis as measured via incorporation of $^3$H-leucine and $^3$H-thymidine, respectively.

It is generally desirable that non-specific binding of the oligomeric molecule to non-target sequences be limited. Although some non-sequence-specific interactions of such oligomers may show therapeutic effects (e.g. Anderson, 1996) such interactions often produce unwanted side effects. To test for non-specific binding, control sequences such as sense or nonsense sequences, or sequences containing mismatched bases, may be included in preliminary screening tests, (in vitro). Excess targeted protein or mRNA may also be added to the cell culture to see if the effect of the antisense oligomer is reversed [Bennett, M. R. et al., *Circulation* 92(7):1981–1993 (1995)].

Additional sequences may be prepared by one of skill in the art, having in mind one or more desired target sequences, with screening carried out according to methods routinely employed by those of skill in the art.

Although targeting of a messenger RNA sequence is preferred, a double-stranded DNA may be targeted by using a non-ionic probe designed for sequence-specific binding to major-groove sites in duplex DNA. Such probe types are described in U.S. Pat. No. 5,166,315 (Summerton and Weller, 1992), which is hereby incorporated by reference, and are also generally referred to herein as antisense oligomers, referring to their ability to block expression of target genes.

Morpholino oligomers can be linked in a polymeric form by stable, uncharged backbone linkages, and can hybridize with a complementary-base target nucleic acid, including target RNA, with high affinity. This combination of properties, which is related to subunit coupling through each morpholino subunit's ring nitrogen, is not found in natural polynucleotides or in polynucleotides containing various charged or uncharged linkages or in polynucleotides containing "one or more" analogs of naturally occurring nucleotides.

According to the present invention, an antisense oligomer may be designed to specifically hybridize to a region of a selected target sequence contained within a target RNA. It will thus be appreciated that the expression product of any gene having a known sequence may be used as a template for the formation of antisense oligomers using routine techniques for synthesis that are known in the art. Such antisense oligos may be incorporated into the methods of the present invention and be used to screen for the expression of target genes. Accordingly, both spliced and unspliced RNA may serve as the template for design of antisense oligomers which may be used in the methods of the invention.

Differences between two or more RNA sequences, e.g., the RNA expressed in two or more biological samples may serve as the basis for synthesis of antisense oligomers which reflect such differences, e.g., a mutation in a particular gene which is preferentially expressed in one tissue and not in another. Such preferential expression may be qualitative or quantitative.

Antisense oligomers having the various linkages described above may be prepared according to known methods. For example, the widely used phosphorothioate-linked oligonucleotide analogs may be prepared on commercial DNA synthesizers, available from Applied Biosystems Inc. or Pharmacia, using standard phosphoramidite or beta-cyanoethyl phosphoramidite chemistry. The phosphite linkages are converted to phosphorothioates by oxidizing with 3H-1,2-benzodithiol-3-one-1,1-dioxide in place of the standard iodine reagent (see, e.g., Agrawal, Smith, Iyer).

III Modes of Practicing the Invention

A. Administering Antisense Oligomers

In one preferred embodiment, the invention provides effective oral delivery of a morpholino antisense compound having uncharged phosphorus-containing backbone linkages contained in a pharmaceutically acceptable carrier which results in hybridization of the oligomer to a mRNA target by Watson-Crick base pairing with a Tm substantially greater than 37° C.

In another preferred embodiment, the invention provides effective oral delivery of the antisense oligomer to the target RNA, such that the determination of the presence or absence of antisense oligomer:RNA heteroduplexes reflects the presence or absence of the target RNA in the subject.

In one aspect of this embodiment, effective delivery may also be accomplished by any of a number of methods known to those of skill in the art to be generally effective for antisense therapy and which result in effective delivery of the antisense oligomer to the target RNA.

In accordance with the invention, such routes of antisense oligomer delivery include, but are not limited to, various systemic routes, including parenteral routes, e.g., intravenous, subcutaneous, intraperitoneal, intramuscular, and intraarterial injection, as well as inhalation and transdermal delivery. In some cases targeted delivery by direct administration to a particular tissue or site is preferred. It is appreciated that any methods which are effective to deliver the drug to a target site or to introduce the drug into the bloodstream are also contemplated.

Targeting of antisense oligomers may also be accomplished by direct injection into a particular tissue or location, i.e., direct injection into a tumor, thereby facilitating an evaluation of expression of a particular RNA sequence associated with the tumor (i.e. a tumor suppressor gene or an oncogene). Alternatively, the antisense oligomer may be conjugated with a molecule which serves to target the oligo to particular tissue or cell type, e.g., an antibody/oligomer conjugate.

Transdermal delivery of antisense oligomers may be accomplished by use of a pharmaceutically acceptable carrier adapted for e.g., topical administration. One molecular conjugate useful for delivering a morpholino is described in PCT patent application WO 97140854, published Nov. 6, 1996, and incorporated herein by reference.

Typically, one or more doses of antisense oligomer are administered, generally at regular intervals for a period of about one to two weeks. Preferred doses for oral administration are from about 1 mg oligomer/patient to about 25 mg oligomer/patient (based on a weight of 70 kg). In some cases, doses of greater than 25 mg oligomer/patient may be necessary. For IV administration, the preferred doses are from about 0.5 mg oligomer/patient to about 10 mg oligomer/patient (based on an adult weight of 70 kg).

The antisense compound is generally administered in an amount and manner effective to result in a peak blood concentration of at least 200–400 nM antisense oligomer. The presence of heteroduplex in a body fluid, e.g., urine is monitored typically 3–18 hours after administration, preferably about 6–12 hours after administration.

IV. Methods of Assaying Antisense Delivery.

A. Detecting Heteroduplexes

In order to serve as an indicator of RNA expression, an antisense oligomer:RNA heteroduplex must have sufficient stability to remain hybridized and resistant to degradation as it passes through the cellular membrane. In particular if the antisense oligomer:RNA heteroduplex is to be detected in the urine, it must also transit through the interstitial fluid into the bloodstream, and be filtered through the kidneys and into the urine. The heteroduplex must thus withstand changes in ionic strength, pH, and temperature, conditions which are known to affect the Tm, and hence, the stability, of most polynucleotide duplexes. These heteroduplexes are detectable and quantifiable in the urine collected from the animals.

In one exemplary assay format for use in urine detection, a sample containing an oligomer:RNA heteroduplex is reacted with a compound that specifically binds to or modifies the oligomer:RNA heteroduplex (e.g., a monoclonal antibody (mAb) specific for the particular heteroduplex) followed by detection of the modified or conjugated oligomer:RNA heteroduplex.

In another exemplary assay format, an antisense oligomer is modified by conjugating it with a reporter molecule before administration to the subject, followed by separation of heteroduplexes from uncomplexed reporter labeled antisense oligomer and detection of the heteroduplex-associated reporter molecule. In some cases such separation may be carried out by via chromatography or electrophoresis.

Exemplary detection methods include spectrophotometric detection (e.g., with a fluorescence detector), or detection using antibodies (e.g., FACS analysis). Such methods may be combined with separation methods in order to expedite analysis, e.g. chromatographic separation with simultaneous fluorescence detection or electrophoretic separation with detection by staining of gels, fluorescence or autoradiographic detection. Such techniques are known to those of skill in the art and readily adaptable to a given antisense oligomer and target RNA sequence.

Any fluorescent molecule known in the art for labeling nucleic acids may be used in the methods of the invention, for example, fluorescein and fluorescein derivatives such as carboxy fluorescein, 5-(4,6-dichlorotriazin-2-yl) amino fluorescein (5-DTAF); eosin; rhodamines such as Texas Red and tetramethylrhodamine; cyanine dyes such as thiazole orange, oxazole yellow and related dyes described in U.S. Pat. Nos. 4,957,870 and 4,888,867; pyrene; porphyrin dyes such as La JollaBlue. The fluorescent label should be selected such that its fluorescent lifetime is comparable in magnitude to the correlation time being measured, taking into account that temperature, viscosity, and the size of the oligonucleotide to which the fluorescent dye is conjugated all affect tumbling time. The fluorescent label is covalently linked or conjugated to the signal primer so as not to interfere with either emission of fluorescence from the label or hybridization of the probe to the target sequence. [See, also, U.S. Pat. No. 5,614,617 and 5,652,099.]

In other cases, antisense oligomers can be synthesized having a sequence complementary to a given target with the 5' end of the sequence attached to a reactive amino group as described by Smith, L. M., et al. Nuc. Acids Res. 13(7):2399 (1985). In such cases, biotin, peptide or an enzyme, e.g., alkaline phosphatase may be attached to the 5' amino group. [See, also U.S. Pat. No. 5,783,391.)

In still another embodiment, the heteroduplex can be detected, e.g., after isolation from the body-fluid sample, by mass spectroscopy. In studies conducted in support of the present invention, it was found that a heteroduplex of RNA:morpholino oligomer is readily resolved into two different-MW fractions (the two heteroduplex strands) by mass spectroscopy. This method thus provides a positive identification of the heteroduplex in terms of its two component strands.

B. Assay Procedures

In one assay method, the heteroduplex is directly detected by the presence of a suitable reporter, or after binding a suitable reporter, e.g., fluorescent-labeled streptavidin to a oligomer binding group, e.g., biotin.

In another approach, a target nucleic acid sequence that is specific to the target nucleic acid, and/or the complement thereof, is selectively increased in copy number, e.g., by PCR. [Saiki et al., Science 230, 1350 (1985); U.S. Pat. Nos. 4,683,195 and 4,683,202.]

In yet another approach, the body fluid sample is reacted with a heteroduplex binding agent, e.g., an antibody that is either reporter labeled or subsequently labeled by binding of a secondary labeled antibody against the primary antibody.

Assays according to the invention may be carried out simultaneously, under conditions as nearly alike as possible, on one or more test samples, and control samples. As understood in the art, control samples are similar to test samples but are known to contain either no target or to lack a particular reagent. Exemplary controls include a sample of the same type of body-fluid from a subject lacking the target RNA and a sample from same subject taken prior to and at one or more time points after administration of an antisense oligomer composition. A control with added target or added oligomer:RNA heteroduplexes may be used to establish the level below which it is not possible to distinguish samples which contain target from those which do not. If control samples having a range of known concentrations of target are employed, the concentration of target in a test sample can be estimated.

A sample on which the assay method of the invention is carried out may be an unprocessed body-fluid sample, such as urine, saliva, plasma, blood or other body fluid, tissue culture medium or food material. In some cases, the method is carried out on a biological sample which has been processed to remove materials that would interfere with detection of target. Methods of processing biological samples to obtain a sample more suitable for the various methods of detecting antisense oligomer:RNA heteroduplexes are well known in the art.

Relevant body fluids containing the sample include urine, plasma (or serum), whole blood, saliva, cerebrospinal fluid and fluid obtained from biopsies tissue. Urine and saliva are preferred body fluids for determining the presence of oligomer:RNA heteroduplexes according to the methods of the invention. A determination of oligomer:RNA heteroduplexes which involves analysis of samples of urine or saliva provides the advantage that such body-fluid samples may be obtained without the need for specialized medical equipment or facilities and with little or no discomfort to the subject. The sample may be pretreated, e.g., by HPLC or electrophoresis to purify or partially purify the heteroduplex prior to its detection or quantitation.

V. Applications of the Method

From the foregoing, it can be appreciated that the compositions and methods of the present invention offer advantages in providing a means for effective oral administration of a class of morpholino antisense oligonucleotides which have from 8 to 40 nucleotides including a targeting base sequence that is complementary to a region that spans the translational start codon of the mRNA of a target gene, and uncharged, phosphorous-containing intersubunit linkages.

The oral administration methods described herein also find utility in determining the presence of expressed target RNAs by delivery of antisense oligomers which can specifically bind to the appropriate target and form oligomer-:RNA heteroduplexes that are readily detectable in body fluids, e.g., urine. It will also be appreciated that the methods described herein have broad applicability to situations wherein it is desirable to determine the presence of RNA in a body fluid of a subject.

The methods of the invention find utility in clinical situations where the condition may be treated with an antisense oligonucleotide. The uncharged morpholino antisense oligomers described herein provide the particular advantage that effective and non-toxic doses may be orally administered in an amount and manner effective to result in a peak blood concentration of at least 200–400 nM antisense oligomer.

The methods of the invention are useful for detection of mRNA produced by expression of any of a number of target genes. Targets of interest are described in detail above and include, but are not limited to, alternatively spliced mRNAs and expressed genes having mutations, insertions, or deletions.

The methods of the invention may also be used to evaluate gene expression which takes place in response to environmental stimuli. For example, expression of the metallothienein gene has been shown to increase in response to exposure to heavy metals, with associated medical implications.

Accordingly, the methods may be used to monitor or treat such exposure by periodic evaluation of metallothienein expression, e.g., in workers in an environment having the potential for heavy metal exposure, by administering antisense oligomers specific to metallothienein RNA to the workers and monitoring the excretion of heteroduplexes comprising metallothienein RNA and one or more antisense oligomers in the urine of the subject. Similarly, the methods of the invention may be used to monitor or treat exposure to any of a number environmental stimuli which are known to result in altered expression of a particular gene.

It will be understood that any of the methods described herein are readily adaptable to a kit format for use in routine monitoring of the expression of a given target RNA.

All patent and literature references cited in the present specification are hereby incorporated by reference in their entirety.

The following examples illustrate but are not intended in any way to limit the invention.

EXAMPLE 1

Formation of Nuclease-Resistant Antisense Oligo:RNA Heteroduplexes in vitro and in vivo In vitro Studies Duplex formation was evaluated by mixing various mRNAs with antisense oligomers, allowing them to hybridize followed by visualization of duplex formation on 12% non-denaturing acrylamide gels run at 36 V for 4.75 hours and stained with ethydium bromide to detect duplex formation and RNAse resistance. The migration of the oligonucleotides in the gel is based on charge to mass and in the case of duplexes, the mass is nearly double that of the RNA alone but no charge is added as the PMO is neutral. The migration of the duplex varies with the acrylamide gel concentration.

An alpha globin synthetic mRNA 25-mer (SEQ ID NO: 1) and a non-complementary PMO oligomer antisense to c-myc (SEQ ID NO:2), or a complementary, alpha globin antisense PMO 25-mer (SEQ ID NO:3) were mixed in the presence or absence of RNAse.

When the alpha globin synthetic 25-mer was mixed with a non-complementary PMO 25-mer having a sequence antisense to c-myc (PMO 1-22- 126, SEQ ID NO:2), only a single band was observed following gel electrophoresis and the molecular weight of the band was consistent with that of the synthetic mRNA 20-mer. However, when the alpha globin synthetic 20-mer was mixed with a complementary, alpha globin antisense PMO 25-mer (SEQ ID NO:3), two bands were observed following gel electrophoresis, a lower band migrating at the predicted rate for the mRNA 25-mer plus a second band migrating at rate predicted for an oligomer of about 200-base pairs. The upper band, but not the lower band, was resistant to treatment with RNAseBM or RNAseT1 prior to loading.

The results indicated that an RNAse resistant duplex was formed between an alpha globin synthetic mRNA 25-mer (SEQ ID NO: 1) and a complementary antisense PMO (SEQ ID NO:3) in the presence of RNAseBM, as indicated by a faint band at the expected gel migration point for a PMO:RNA duplex and no band for the RNA alone.

The results further indicated that an RNAse resistant duplex was formed between an alpha globin synthetic mRNA 25-mer (SEQ ID NO: 1) and a complementary antisense PMO (SEQ ID NO:3) in the presence of RNAseT1, as indicated by a band at the expected gel migration point for a PMO:RNA duplex and no band for the RNA alone, indicating the RNA can be degraded when not part of the duplex.

A comparison of the results of electrophoresis with mixtures of complementary versus non-complementary mRNA:antisense oligomer pairs confirmed that a duplex forms between mRNA and its complementary antisense PMO oligomer, that the duplex is resistant to degradation by RNAse. The relative gel electrophoresis migration rate of mixtures of complementary mRNA:antisense oligomer pairs in the presence and absence of RNAse, show that a duplex forms between an alpha globin synthetic mRNA 25-mer (SEQ ID NO: 1) and a complementary antisense PMO (SEQ ID NO:3) and that excess alpha globin synthetic mRNA is present in the absence of RNAse.

In vivo Studies

Antisense oligomers were injected intraperitoneally into rats followed by formation of stable oligomer:RNA heteroduplexes in vivo which were subsequently detectable in rat urine.

For each test animal, one ml of urine collected 24 hours following administration, was dialyzed against a standard assay buffer in 6000 to 8000 mw cutoff dialysis tubing (Spectra/Por) to remove salts. The dialyzed samples were incubated with DNAse and RNAseH for 10 minutes and dried in a Savant Speed-Vac. Dried samples were dissolved in 50 µl water and 25 µl was loaded per lane onto a 12% non-denaturing acrylamide gel.

Rats were administered saline, or 3 nmoles, 75 nmoles or 375 nmoles of the PMO 1-22-126 20 mer antisense to c-myc (SEQ ID NO:2) at the time of partial hepatectomy. The results of gel electrophoresis show the presence of a DNAse and RNAse-resistant band which migrates near the 200 bp DNA ladder band, consistent with that of a PMO:RNA heteroduplex. Appearance of this band is dependent on the amount of PMO administered, and is absent when rats are injected with saline. In rats given 375 nmoles of the PMO 1-22-126 20 mer antisense to c-myc (SEQ ID NO:2) at the time of partial hepatectomy a band is observed which is consistent with the migration pattern of a PMO:RNA duplex, which supports the detection of a PMO:RNA duplex following in vivo exposure to the PMO.

These observations support the formation in vivo of a specific, detectable antisense oligomer:RNA heteroduplex upon administration of a PMO to an animal. This heteroduplex forms intracellularly and remains resistant to nucleases and stable to changes in osmolality throughout its transit through the cell membrane into the renal blood supply, its clearance through the kidneys into the urine.

EXAMPLE 2

In vivo Studies with Antisense Oligomer:RNA Heteroduplexes

Calibration studies performed using an instrument capable of detecting fluorescein conjugated oligomers (Applied Biosystems Model 672 GeneScanner) were used to determine the migration rates of fluorescein-conjugated oligomers of various lengths; a 15-mer, a 20-mer, a 24-mer and a 38-mer ribozyme. Migration rates were evaluated on a GeneScanner gel and calibration studies confirmed the validity of the GeneScanner approach to detection of PMO:RNA duplexes. Calibration studies show that the Applied Biosystems Model 672 GeneScanner can distinguish fluorescein conjugated oligomers on the basis of both length and concentration.

In vivo Studies

Rats were injected intraperitoneally, as in Example 1, with a carboxyfluorescein-conjugated PMO (SEQ ID NO:5), which is antisense to rat cytochrome P-4503A2 (SEQ ID NO:6).

GeneScanner chromatograms of plasma samples prepared from blood withdrawn from rats one hour post-injection contained fluorescent components which migrated at 270 and 340 minutes (two peaks due to the two possible carboxyfluorescein linkages which migrate differently). Plasma samples prepared from rats 24 hours post-injection contained fluorescent components which migrated at approximately 75 and 80 minutes. Mass spectral data (not shown) confirms that the shorter migration time is not due to degradation of the PMO and indicates that a PMO:RNA heteroduplex has been formed over that time.

Figure 3:
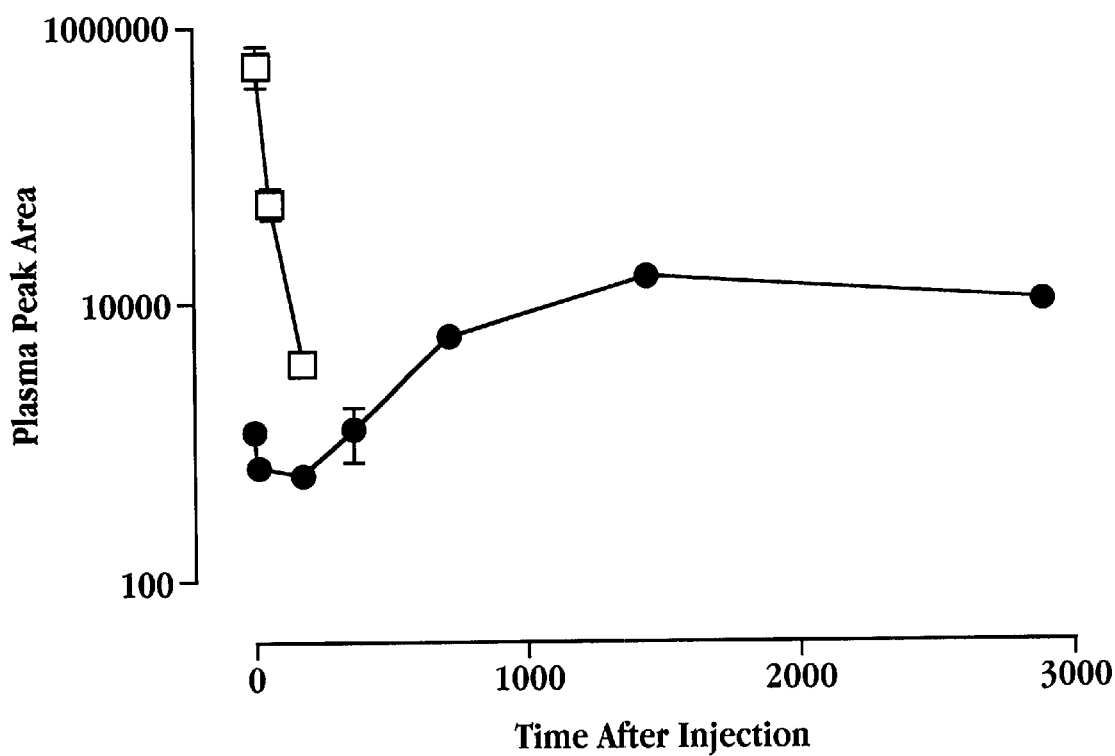
FIG. 3 is a kinetic representation of the disappearance of PMO monomer and appearance of RNA:PMO heterodimer in the plasma of rats administered the P450 antisense phosphorodithioate morpholino oligomer over time (minutes). The open boxes correspond to phosphorodithioate morpholino oligomer monomer and the closed circles correspond to RNA:phosphorodithioate morpholino oligomer dimer.

FIG. 3 represents the results of an analysis of samples taken at various times post administration of the P450 antisense PMO, and indicates the disappearance of the PMO monomer and the corresponding appearance of RNA:PMO heterodimer in the plasma of rats following such administration. Appearance of significant quantities of the duplex in plasma does not occur until the majority of the unduplexed PMO leaves the plasma in what is generally referred to as the "distribution phase". The PMO heteroduplex does not accumulate in plasma until after PMO monomer has distributed into the tissues of the subject where the complementary mRNA transcripts are localized. The charged RNA:PMO duplex presumably forms in these tissues and effluxes out of cells and back into plasma. This overall process requires several hours.

After administration of the p450 antisense PMO (SEQ ID NO:5), fluorescein was detected in both the kidney and liver.

Chromatograms of kidney tissue samples showed a band at 350 minutes consistent with unduplexed PMO and an additional band at 80 minutes consistent with the PMO:RNA heteroduplex, indicating both duplex and parent PMO which may reside in interstitial spaces or within the cells of the kidney. The liver tissue sample showed essentially no unduplexed PMO and significantly more PMO:RNA heteroduplex. These results are consistent with the observation that levels of P450 mRNA transcript are much lower in kidney than in liver.

Studies reflecting the time course of urinary clearance of unduplexed antisense PMO oligomer and antisense PMO oligomer:RNA heteroduplexes indicate that several hours are required for formation and efflux of PMO:RNA heteroduplex from tissues into plasma, followed by their ultimate appearance in urine.

Although the invention has been described with reference to specific methods and embodiments, it will be appreciated that various modifications and changes may be made without departing from the invention.

| Description | SEQ ID NO |
|---|---|
| synthetic 25-mer corresponding to alpha globin mRNA (5'-CCA GUC CGU CUG AGA AGG AAC CAC C-3') | 1 |
| PMO 25-mer antisense to c-myc (nt 1-22-126; 5'-ACG TTG AGG GGC ATC GTC GC-3') | 2 |
| PMO 25-mer antisense to alpha globin mRNA 5'-GGU GGU UCC U UC UCA GAC GGA CUG G-3' | 3 |
| PMO antisense to rat cytochrome P-4503A2 (1-0-256; 5'-UGA GAG CUG AAA GCA GGU CCA U-3') | 4 |
| carboxyfluorescein conjugated PMO complementary (antisense) to rat cytochrome P-4503A2 (1-0-256) 5'-U ACC UGG ACG AAA GUC GAG AGU-3' | 5 |
| rat cytochrome P-4503A2 5'-ACT CTC GAC TTT CGT CCA GGT A-3' | 6 |

It is claimed:

1. A method of detecting in a subject, the occurrence of a base-specific intracellular binding event involving a target mRNA produced by expression of a selected gene, comprising
   (a) administering to the subject a morpholino antisense oligomer compound having (i) from 8 to 40 nucleotides, including a targeting base sequence that is complementary to a region of the target mRNA, and (ii) uncharged, phosphorous-containing intersubunit linkages, in an amount effective to hybridize by Watson-Crick base pairing to a region of the target RNA with a Tm substantially greater than 37° C.,
   (b) at a selected time after said administering, taking a sample of a body fluid from the subject, and
   (c) detecting in said sample the presence of a nuclease-resistant heteroduplex composed of the antisense oligomer and said target RNA region.

2. The method of claim 1, wherein the body fluid is urine.

3. A kit for detecting the presence of a base-specific intracellular binding event involving a target mRNA produced by expression of a selected gene, comprising:
   (a) a morpholino antisense compound having (i) from 8 to 40 nucleotides, including a targeting base sequence that is complementary to a region of the target mRNA, and (ii) uncharged, phosphorous-containing intersubunit linkages, in an amount effective to hybridize by Watson-Crick base pairing to a region of a target RNA with a Tm substantially greater than 37° C.; and
   (b) means for detecting a heteroduplex formed between the antisense oligomer and the target RNA.

* * * * *

SEQUENCE LISTING

<160> NUMBER OF SEQ ID NOS: 6

<210> SEQ ID NO 1
<211> LENGTH: 25
<212> TYPE: RNA
<213> ORGANISM: Artificial Sequence
<220> FEATURE:
<223> OTHER INFORMATION: alpha globin mRNA synthetic 25-mer

<400> SEQUENCE: 1
ccaguccguc ugagaaggaa ccacc                                    25

<210> SEQ ID NO 2
<211> LENGTH: 20
<212> TYPE: DNA
<213> ORGANISM: Artificial Sequence
<220> FEATURE:
<223> OTHER INFORMATION: antisense

<400> SEQUENCE: 2
acgttgaggg gcatcgtcgc                                          20

<210> SEQ ID NO 3
<211> LENGTH: 25
<212> TYPE: RNA
<213> ORGANISM: Artificial Sequence
<220> FEATURE:
<223> OTHER INFORMATION: antisense

<400> SEQUENCE: 3
ggugguuccu ucucagacgg acugg                                    25

<210> SEQ ID NO 4
<211> LENGTH: 22
<212> TYPE: RNA
<213> ORGANISM: Artificial Sequence
<220> FEATURE:
<223> OTHER INFORMATION: antisense

<400> SEQUENCE: 4
ugagagcuga aagcaggucc au                                       22

<210> SEQ ID NO 5
<211> LENGTH: 22
<212> TYPE: RNA
<213> ORGANISM: Artificial Sequence
<220> FEATURE:

-continued

```
<223> OTHER INFORMATION: antisense

<400> SEQUENCE: 5
uaccuggacg aaagucgaga gu                                              22

<210> SEQ ID NO 6
<211> LENGTH: 22
<212> TYPE: DNA
<213> ORGANISM: rat

<400> SEQUENCE: 6
actctcgact ttcgtccagg ta                                              22
```